United States Patent
Furey et al.

(10) Patent No.: US 7,896,197 B2
(45) Date of Patent: Mar. 1, 2011

(54) FLUID DISPENSING DEVICE

(75) Inventors: James F. Furey, Brookline, MA (US); Mark McInnes, Wayne, PA (US)

(73) Assignee: Millipore Corporation, Billerica, MA (US)

( * ) Notice: Subject to any disclaimer, the term of this patent is extended or adjusted under 35 U.S.C. 154(b) by 192 days.

(21) Appl. No.: 10/992,877

(22) Filed: Nov. 19, 2004

(65) Prior Publication Data

US 2005/0109795 A1    May 26, 2005

Related U.S. Application Data

(60) Provisional application No. 60/523,625, filed on Nov. 20, 2003.

(51) Int. Cl.
*B67D 1/00* (2006.01)

(52) U.S. Cl. .............................................. 222/64; 222/92

(58) Field of Classification Search .................... 222/63, 222/64, 55, 206–215, 68, 69, 71–73, 1, 20, 222/92–107; 210/192.8, 110, 137
See application file for complete search history.

(56) References Cited

U.S. PATENT DOCUMENTS

| | | | |
|---|---|---|---|
| 2,412,397 A | 12/1946 | Harper | |
| 2,909,125 A | 10/1959 | Daniels | |
| 4,030,640 A * | 6/1977 | Citrin et al. | 222/207 |
| 4,240,408 A * | 12/1980 | Schael | 604/28 |
| 4,275,726 A * | 6/1981 | Schael | 604/6.06 |
| 4,528,158 A | 7/1985 | Gilles et al. | |
| 4,712,590 A * | 12/1987 | Gianfilippo | 141/83 |
| 5,090,594 A | 2/1992 | Randall et al. | |
| 5,165,873 A | 11/1992 | Meijer | |
| 5,174,474 A * | 12/1992 | Tammi et al. | 222/94 |
| 5,203,367 A | 4/1993 | Akai et al. | 136/101.25 |
| 5,234,608 A * | 8/1993 | Duff | 210/806 |
| 5,405,443 A * | 4/1995 | Akimoto et al. | 118/668 |
| 5,480,063 A | 1/1996 | Keyes et al. | 222/64 |
| 5,664,990 A * | 9/1997 | Adams et al. | 451/60 |
| 5,680,960 A | 10/1997 | Keyes et al. | 222/64 |
| 5,697,407 A * | 12/1997 | Lasonde | 141/104 |
| 5,698,090 A * | 12/1997 | Bene et al. | 210/85 |
| 5,709,539 A | 1/1998 | Hammer et al. | |
| 5,980,490 A | 11/1999 | Tsoukalis | |
| 6,024,251 A * | 2/2000 | Mayer et al. | 222/64 |
| 6,036,166 A * | 3/2000 | Olson | 251/7 |
| 6,062,829 A | 5/2000 | Ognier | |
| 6,202,708 B1 | 3/2001 | Bynum | |
| 6,726,771 B2 * | 4/2004 | Ueda | 118/633 |
| 7,104,422 B2 * | 9/2006 | DiLeo | 222/64 |
| 7,128,242 B2 * | 10/2006 | Erlandsen | 222/95 |

FOREIGN PATENT DOCUMENTS

| | | |
|---|---|---|
| EP | 0058292 | 8/1982 |
| EP | 1145727 | 10/2001 |

OTHER PUBLICATIONS

"Acerta Disposable Filling System", Millipore Product Brochure, Lit. No. PF 1200EN00 (Dec. 2002).
U.S. Appl. No. 10/635,124, filed by B. Belongia et al. on Aug. 6, 2003, entitled "Fluid Dispenser Cartridge".

* cited by examiner

*Primary Examiner* — Lien T Ngo

(57) ABSTRACT

A fluid dispensing device, suitable for dispensing fluid from a fluid supply to a receptacle, is disclosed, wherein a pliable fluid reservoir is located between the fluid supply and the receptacle, and wherein peristaltic pumps are used to supply and dispense said fluid from the pliable fluid reservoir. The fluid level in the pliable fluid reservoir is electronically monitored with data being transmitted to either or both pumps for the operative control thereof. The pliable fluid reservoir is configured, together with certain connected conduits, as a disposable, easily-installable, single-use unit.

20 Claims, 4 Drawing Sheets

FLUID DISPENSING DEVICE

REFERENCE TO RELATED APPLICATION

The present application claims the benefit of U.S. Provisional Patent Application Ser. No. 60/523,625, filed on Nov. 20, 2003.

FIELD

In general, the present invention is directed to fluid dispensing devices, and in particular, to a fluid dispensing device incorporating a "single-use" pliable fluid reservoir electronically linked to peristaltic fluid pumping mechanisms.

BACKGROUND

Numerous types of fluid dispensing apparatuses exist for filling bottles. One type of fluid dispensing apparatus which is in widespread use is a positive displacement filler. Positive displacement fillers typically include moving parts which contact and displace the fluid being dispensed. For example, one type of positive displacement filler uses a piston and cylinder arrangement. In this type of positive displacement filler, the backward movement of the piston draws fluid into the cylinder through an inlet port and the forward movement of the piston expels the fluid through an outlet port. Another type of positive displacement filler uses a rotary pump to move the fluid.

Positive displacement pumps have gained widespread use in the United States for two reasons. First, positive displacement pumps can operate at relatively high speeds, filling as many as six hundred bottles per minute. Additionally, positive displacement pumps are accurate up to about ±0.5%.

Despite the widespread use of positive displacement fillers, they nevertheless have disadvantages. One disadvantage with positive displacement fillers is that fluid comes into contact with moving parts. As the moving parts wear, particulate matter enters the fluid causing particulate contamination. If severe enough, particulate contamination can render the product unusable. Another disadvantage involves the difficulty in cleaning and sterilizing the moving parts in contact with fluid. In positive displacement pumps, the critical tolerances between parts, such as the piston and cylinder, precludes effective cleaning without disassembly. Disassembly is not only time consuming, but can result in biological contamination of the parts when they are handled during re-assembly.

Another type of fluid dispensing apparatus is the time/pressure filler. A typical time/pressure filler includes a fluid reservoir which is maintained under a relatively constant pressure. The fluid is dispensed from the reservoir through a compressible discharge line. Fluid flow is shut off by a pinch type valve which squeezes and collapses the discharge line. A pre-determined volume of fluid is dispensed by opening the discharge line for a pre-determined period of time. If the pressure within the fluid reservoir is maintained constant, an equal amount of fluid should be dispensed each time the cycle is repeated.

Another type of fluid dispensing apparatus, i.e., a volumetric fluid dispensing apparatus, is shown in U.S. Pat. No. 5,090,594. A volumetric dispensing apparatus measures a predetermined volume of fluid in a measuring cup or fill tube which is subsequently dispensed into a receptacle. Volumetric fillers, while slower than positive displacement fillers, are highly accurate and better avoid the problems of microbial and particulate contamination. Volumetric fillers, like time/pressure fillers, depend on a relatively constant pressure.

Another type of fluid dispensing apparatus is described in U.S. Pat. No. 5,480,063, issued to Keyes et al. on Jan. 2, 1996. Keyes et al. describe an apparatus having no moving parts in contact with the fluid being dispensed. The fluid-dispensing apparatus includes a fluid chamber containing the fluid to be dispensed and a fill tube communicatively connected to the fluid chamber. The fill tube forms a circuit with the fluid reservoir. In operation, fluid is transferred from the chamber into the fill tube. When the fluid level in the fill tube reaches a predetermined height, filling is terminated and fluid dispensed from the fill tube into a container. See also, U.S. Pat. No. 5,680,960, issued to Keyes et al. on Oct. 28, 1997.

Despite the approaches embodied in the technologies above, there is a continuing need for improvements to and/or alternative configurations for fluid dispensing apparatuses, particularly one implementing disposable single-use, fluid handling components.

SUMMARY

In response to the above need, the present invention provides a fluid dispensing device 10, wherein fluid is feed into and dispensed from a "single-use" pliable fluid reservoir 60 by means of, respectively, a supply-side peristaltic pump 40 and a dispense-side peristaltic pump 50.

Sensing means 12 are employed to detect the fluid level in the pliable fluid reservoir 50. An electronic controller 90 transmits and receives signals to and from the sensing means, and to and from either one of or both peristaltic pumps 40 and 50. Information carried on said signals is processed by the electronic controller 90, and appropriate signals sent to these (and possibly other) device components to thereby control the conduct of fluid dispensation.

In a particular embodiment, the fluid dispensing device comprises: a pliable fluid reservoir having a fluid inlet and a fluid outlet; a supply-side conduit connected to the fluid inlet; a dispense-side conduit connected to the fluid outlet; sensing means placed proximate the pliable fluid reservoir, said sensing means capable of detecting the fluid level in the pliable fluid reservoir and transmitting data thereabout; a supply-side peristaltic pump engaged onto the supply-side conduit; a dispense-side peristaltic pump engaged onto the dispense-side conduit; and an electronic controller capable of controlling the supply-side and/or the dispense-side peristaltic pumps based on data received from said sensing means.

In light of the above, it is a principal object of the present invention to provide a fluid dispensing device utilizing peristaltic pumps for supplying and dispensing fluid from pliable fluid reservoir.

It is another principal object of the present invention to provide a fluid dispensing device that utilizes peristaltic pumps to supply and dispense fluid from a pliable fluid reservoir, wherein said pliable fluid reservoir is part of a single-use disposable unit which is engaged in use to said pumps.

It is another object of the present invention to provide a fluid dispensing device that utilizes peristaltic pumps to supply and dispense fluid from a pliable fluid reservoir, wherein the operation of said peristaltic pumps is controlled based on fluid level data electronically sensed from said pliable fluid reservoir.

Other object of the present invention will become apparent from the following detailed description taken in conjunction with the accompanying drawings.

DETAILED DESCRIPTION

Figure 1:
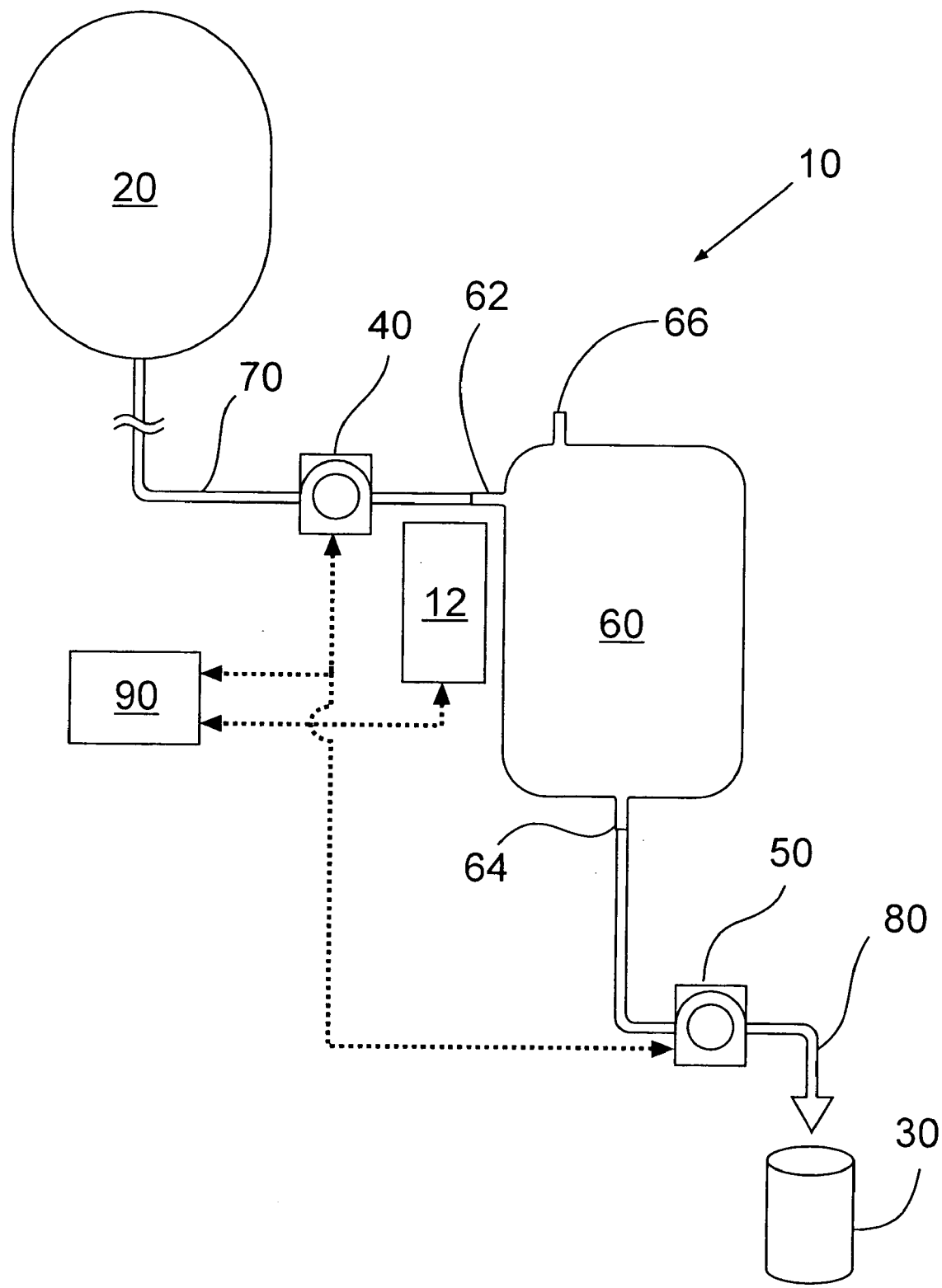
FIG. 1 illustrates schematically a fluid dispensing device 10 according to a "single head" embodiment of the present invention.
Figure 2:
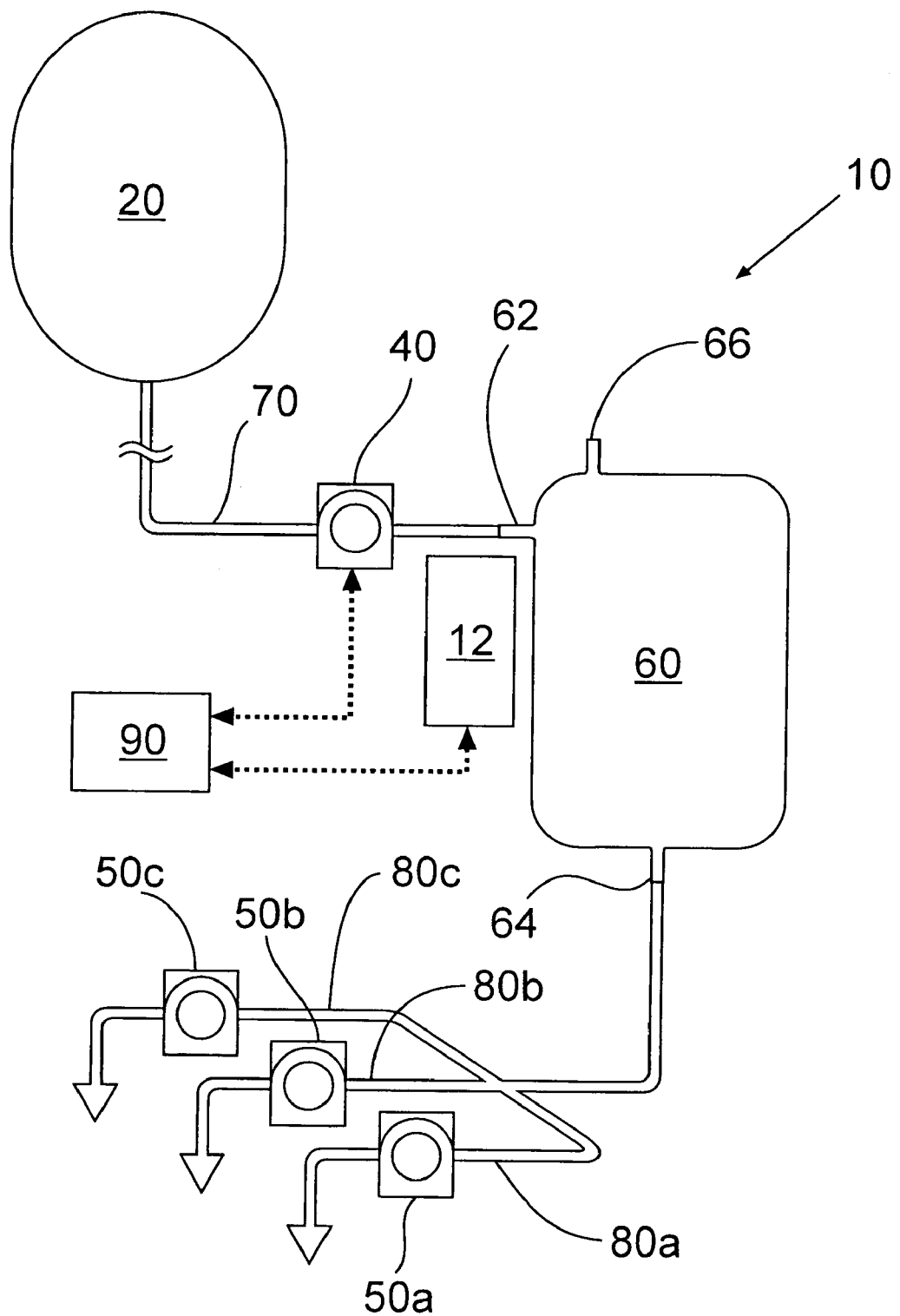
FIG. 2 illustrates schematically a fluid dispensing device 10 according to a "multiple head" embodiment of the present invention.

Referring to FIG. 1, the present invention provides a fluid dispensing device 10 that can be used to dispensed fluid from a fluid supply 20 to a receptacle 30. The fluid dispensing device includes a pliable fluid reservoir 60 that has a fluid inlet 62 and a fluid outlet 64. A "supply-side" conduit 70 and a "dispense-side" conduit are connected, respectively, to the fluid inlet 62 and the fluid outlet 64 of the pliable fluid reservoir 64, with the supply-side conduit being connectable to said fluid supply 20. Each of the conduits are engaged or capable of being engaged into respective supply-side and dispense-side peristaltic pumps 40 and 50. Sensing means 12 are placed proximate the pliable fluid reservoir 60 to enable detection of the fluid level therein and to transmit or otherwise electronically provide data thereabout. An electronic controller 90 is provided to receive said data, and on the basis thereof, control the operation of either one of or both the supply-side and dispense-side peristaltic pumps 40 and 50.

The pliable fluid reservoir 60 as indicated is provided with at least a fluid inlet 62 and a fluid outlet 64, the fluid inlet and outlet having dimensions, locations, and constructions suitable for introducing and releasing fluid into and out of the fluid reservoir, respectively. The fluid inlet 62 can be located in the upper or lower half of the pliable fluid reservoir 60. The fluid outlet 64 is generally located in the lower half of the pliable fluid reservoir 60, preferably in an area that enables optimum and/or essentially complete fluid drainage.

The pliable fluid reservoir 60 provides functionality comparable to so-called "surge tanks"—rigid containers often used in industrial fluid dispenser between a larger volume fluid supply container and a dispense head. Regardless, the pliable fluid reservoir 60 also provides fluid pressure control of a character and quality beyond the capacity of rigid surge tanks, while having a construction amenable to single-use disposability. Along these lines, the relative size and location of a pliable fluid reservoir 60, when installed into a fluid dispensing device 10, is selected to effect favorably both upstream and downstream fluid pressure conditions, and thereby yield fast and accurate fluid dispensation.

In the interest of reducing manufacturing costs, the pliable fluid reservoir 60 ca be of substantially unitary construction, having a minimum number of assembled parts, seams, welds, and integrated sub-components, for example, a bag of durable single-layer construction or the like.

The "pliability" of the pliable fluid reservoir 60 will vary among different applications, being influenced by such things as the expected external pressure, the rheological properties of the dispensed sample fluid, the configuration and internal volume of any implemented dispense-side conduit manifold assembly, and the like. The chemical properties of the fluid will likely influence the type of materials that can be used to make the pliable fluid reservoir, for example, certain fluids may require the use of less pliable, durable materials. Regardless, the balance between durability and pliability is felt within the skill in the art.

In preferred practice, the pliable fluid reservoir 60 is combined in construction with the supply-side conduit 70 and the dispense-side conduit 80, forming a disposable single-use "cartridge" (cf., a "consumable") that can be easily installed prior to use into the other fixed "hardware" components of the fluid filtration device 10. The supply-side conduit 70 is attached to the pliable fluid reservoir 60 at its fluid inlet 62. The dispense-side conduit 80 is attached to pliable fluid reservoir 60 at its fluid outlet 64. If desired, a filter element (not shown) can be integrated into the supply-side conduit at a location either upstream or downstream of the location reserved for the supply-side peristaltic pump 40.

There is no particular limitation to the construction of conduits 70 and 80, other than that they be sufficiently pliable, flexible, and/or compressible to allow fluid to be sequentially "squeezed" therethrough by peristaltic pumps 40 and 50. In embodiments of fluid dispensing device 10, both the supply-side and dispense-side conduits 70 and 80 comprise flexible, substantially biologically inert, synthetic polymeric tubing having an internal diameter of approximately 0.100 inches (0.254 cm). Both conduits 70 and 80 can be integral with, fused to, welded to, or otherwise permanently connected to the pliable fluid reservoir 20.

As an alternative to constructing a "single-head" dispense conduit, the fluid dispensing device 10 can employ a manifold assembly 68 to subdivide the dispense-side conduit 80 into a plurality of sub-branches 80a, 80b, and 80c. To control flow, each conduit sub-branch is provided with its own peristaltic pump 50a, 50b, and 50c. Alternatively, a single peristaltic pump can be engaged onto dispense-side conduit 80 prior to the branching thereof by the manifold assembly 68, with the control of flow through each sub-branch 80a, 80b, and 80c enabled by the use of electronically-controllable pinch valves (not shown) engaged thereonto. The former construction (i.e., multiple pumps) is preferred to the extent that the potentially complex synchronization of valve and pump activation and deactivation is avoided.

For pharmaceutical and other sterile applications, the discharge end (i.e., "head") of the dispense-side conduit 80 is preferably fitted, for example, with a hermetically-enclosed syringe needle (not shown) to enable aseptic fluid dispensation from the pliable fluid reservoir 60 into, for example, a septum-capped vial or like receptacle.

Examples of suitable polymeric material for the pliable fluid reservoir and the conduits 70 and 80 include, but are not limited to, polycarbonates, polyesters, nylons, PTFE resins and other fluoropolymers, acrylic and methacrylic resins and copolymers, polysulphones, polyethersulphones, polyarylsulphones, polystryenes, polyvinyl chlorides, chlorinated polyvinyl chlorides, ABS and its alloys and blends, polyurethanes, thermoset polymers, polyolefins (e.g., low density polyethylene, high density polyethylene, and ultrahigh molecular weight polyethylene and copolymers thereof), polypropylene and copolymers thereof, and metallocene generated polyolefins.

In conducting fluid dispensation with the inventive apparatus, the maintenance of appropriate internal pressure conditions is important. As fluid moves to and from the pliable fluid reservoir, gas pressure within can fluctuate if not controlled, and thus lead to inaccuracies in dispensed volumes, which is unacceptable, for example, when the product dispensed is to be an accurate dosage of pharmaceutical product. For the present invention, appropriate internal pressure conditions can be promoted by the installation of the gas gating means 66 to maintain atmospheric pressure throughout the assembly.

The structure, location, and configuration of the gating means 66 is subject to variation, depending on such factors as, intended application and the structure of the pliable fluid reservoir 60, such as its internal dimensions, and the number of dispense-side conduit heads. Two principal embodiments, however, are a vent filter assemblage and a pressure-activated valve. Of these two mechanisms, the vent filter—in consideration of its potentially lower implementation costs—is particularly preferred.

In respect of the vent filter assemblage, a representative embodiment comprises a structure molded into or installed onto the pliable fluid reservoir 60 above the expected maximum fluid level and that forms thereon an inlet and an outlet, with a passage therebetween, and a membrane or filter cross-sectionally dividing said passage.

Although not a limit to the present invention, in respect of the dispensing of pharmaceutical fluids, the total internal volume of pliable fluid reservoir 60 as currently embodied is in the range of about 1.5 liters to about 10 liters. With such volumes, the dimensions of the supply inlet, optional vent outlet, and fluid output are as follows: The diameter of the supply inlet ranges from about 0.25 inch to about 0.75 inch (about 0.635 cm to about 1.90 cm); the diameter of the vent outlet ranges from about 0.125 inch to about 0.75 inch (about 0.3175 cm to about 1.90 cm); and the diameter of the fluid outlet ranges from about 0.125 inch to about 0.75 inch (about 0.3175 cm to about 0.1.90 cm). For greater volumes—particularly, when involving viscous fluids—these dimensions may be substantially larger.

As indicated, a pair of peristaltic pumps 40 and 50 are engaged onto the supply-side conduit 70 and dispense-side conduit, respectively. In operation, the supply-side peristaltic pump 40 provides the peristaltic urging force that enables flow of sample liquid from the fluid supply 20 into the pliable fluid reservoir 60. Likewise, the dispense-side peristaltic pump 50 provides the peristaltic urging force that enables flow of sample liquid from the pliable fluid reservoir 60 ultimately out of the fluid dispensing device 10 into an appropriate receptacle 30. Both pumps 40 and 50 enable aseptic peristaltic flow and do not require for installation the severing of either conduit. The flow of sample liquid through the conduits remains physically isolated from the outside ambient environment and the pump mechanisms.

The placement of the peristaltic pumps 40 and 50 along the conduits 70 and 80 is not categorically critical to the practice of the invention. Although both will likely be placed roughly "midway" positions, other contemplated embodiments of the invention will vary in the location of the pumps 40 and 50. Certain embodiments will benefits in placing the pumps exactly midway of their respective conduits; some embodiments, may locate one (or both) closer to the pliable fluid reservoir; others, farther. Factor that may effect pump placement include, but are not limited to, the volume capacity of the fluid supply 20, the volume capacity of the pliable fluid reservoir 60, the length and diameter of the conduits 70 and 80, the viscosity and constituency of targeted sample liquids, the operating range of the selected peristaltic pumps 40 and 50, and/or the desired accuracy and/or dispense rate of the fluid dispensing device 10.

Figure 3A:
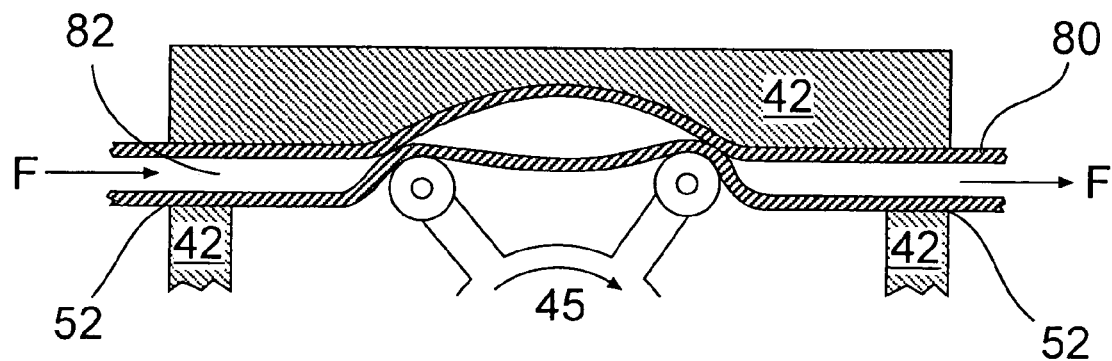
FIG. 3a illustrates schematically certain operative features of a rotary peristaltic pump.
Figure 3B:
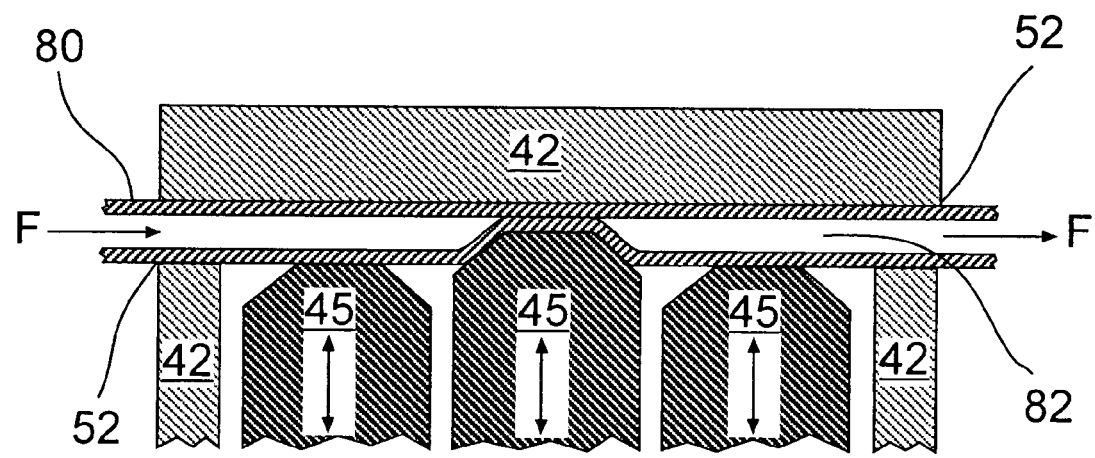
FIG. 3b illustrates schematically certain operative features of a linear peristaltic pump.

The particular mechanical structure of the peristaltic pumps 40 and 50—like their placement—is also not critical to the practice of the invention. Regardless, as illustrated in FIGS. 3A and 3B, useful peristaltic pumps will generally comprise, disposed within a housing 42, a channel 52 and peristaltic pinching means 45. In operation, a conduit 80 (or 70) is engaged within channel 52. Peristaltic pinching means 45 is then activated to sequentially pinch the conduit 80 along a length thereof, collapsing the lumen 82 in a wavelike motion, and sequentially displacing sample liquid therein along flow path F.

Peristaltic pumps are generally one of two types, namely rotary peristaltic pumps and linear peristaltic pumps, illustrated in FIGS. 3A and 3B, respectively. In the rotary peristaltic pump shown in FIG. 3A, the peristaltic pinching mean 45 applies force in a sweeping circular or arcuate motion. In particular, the pinching force is applied by "fingers" of rotating drum that sequentially pinch the conduit 80 against an arcuate channel 52. In the linear peristaltic pump shown in FIG. 3B, the peristaltic pinching means 45 applies force in a series of linear, punctuated motions. In particular, the pinching force is applied by a series of linearly reciprocating fingers—often disposed on a cam shaft—that orthogonally meet and pinch sequential portions of the conduit 80. Other linear mechanisms are available, for example, a linearly displaceable pinch valve.

In constructing the inventive fluid dispensing device, the supply-side peristaltic pump 40 and dispense-side peristaltic pump 50 can be same or different in respect of type and/or capacity. For example, one can be linear and the other rotary. Or they can be both linear or both rotary. Or one may perform more accurately than the other. Regardless, in the currently preferred device, to facilitate both construction and ease of operation, both pumps 40 and 50 are identical.

Further details and alternative embodiments of rotary peristaltic pumps can be found, for example, in U.S. Pat. No. 2,909,125, issued to P. J. Daniels on Oct. 20, 1959; U.S. Pat. No. 5,709,539, issued to M. R. Hammer et al. on Jan. 20, 1998; and U.S. Pat. No. 6,062,829, issued to J.-F. Ognier on May 16, 2000. Further details and alternative embodiments of linear peristaltic pumps can be found, for example, in U.S. Pat. No. 2,412,397, issued to L. E. Harper on Dec. 10, 1946; U.S. Pat. No. 5,165,873, issued to R. S. Meijer on Nov. 24, 1992; and U.S. Pat. No. 5,980,490, issued to A. Tsoukalis on Nov. 9, 1990.

In respect particularly of the construction and/or selection of the dispense-side peristaltic pump 50, comparatively heightened consideration is given to pump's capacity to stop the flow of sample fluid therethrough when inactive. In this regard, it will be appreciated that, in a preferred embodiment, of the present invention, a supplemental discharge valve or gate (e.g., a pinch valve) is not used on the dispense-side conduit 80 between the pump 50 and the conduit 80's outlet. Hence, the flow of sample liquid out of the fluid dispensing device into receptacle 30 is variably controlled—in respect of active and inactive sample flow rate and volume—exclusively by the dispense-side peristaltic pump 50. Provided with an appropriately liquid-tight peristaltic pump, such configuration facilitates construction, maintenance, and operation, while still providing good fluid dispensation with little to no dripping.

As indicated, sensing means 12 are installed or otherwise provided proximate the pliable fluid reservoir 60 to enable the detection of level or volume of fluid contained therein. The sensing means can accomplish detection optically, sonically, electronically, or by weight. Fluid volume detection through such avenues are known, and can be incorporated as desired.

Figure 4:
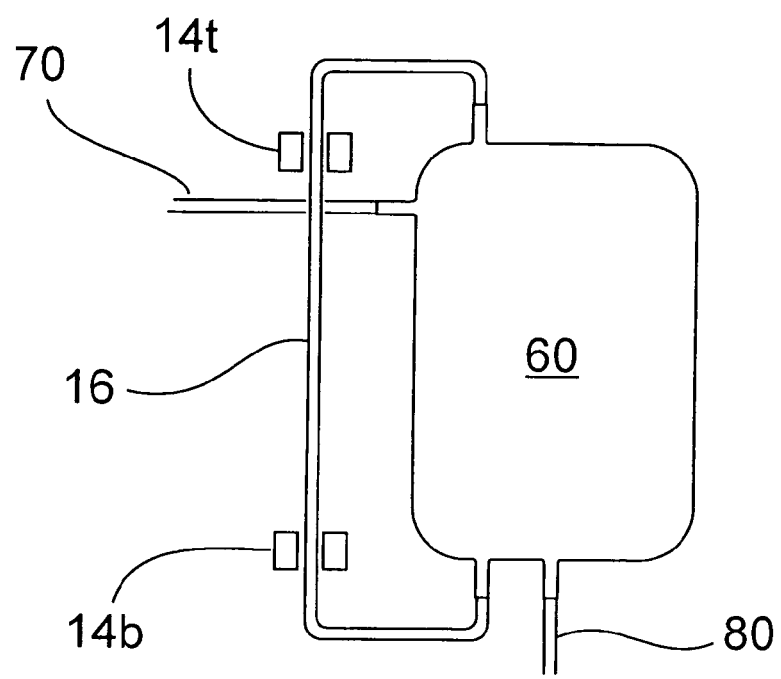
FIG. 4 illustrates schematically optical fluid level sensing mean $14_A$, $14_B$, 16, said means being suitable for incorporation into embodiments of a fluid dispensing device.
Figure 5:
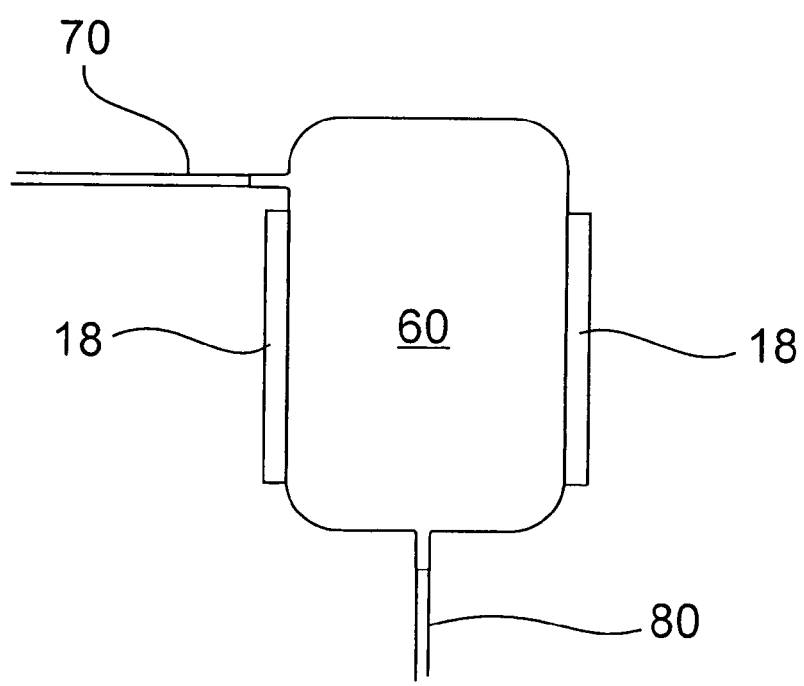
FIG. 5 illustrates schematically electronic fluid level sensing means 18, said means being suitable for incorporation into embodiments of a fluid dispensing device.

By way of example, FIG. 4 and FIG. 5 provide representative schematic embodiments of an optical and an electronic sensing means, respectively.

Although it is possible to employ optical sensing means focussed directly upon the pliable fluid reservoir 60, the pliability of said reservoir—and the likelihood that its shape (and hence internal volume) may change during fluid dispensation—argue in favor of taking an indirect approach. Towards such end, as shown in FIG. 4, the optical sensing means is configured to comprise: a side tube 16 connected to and in "fluid communication" with the pliable fluid reservoir 60; and a plurality of optical detectors $14_T$ and $14_B$ located to detect attainment of certain user-definable top and bottom fluid levels, respectively, along said side tube 16. The optical detectors $14_T$ and $14_B$ provide electronic signal indicative of the water level in the side tube 16, which correlate with the fluid level in the pliable fluid reservoir 60.

For certain applications, the volume of fluid in the pliable fluid reservoir 60 is a key consideration in practicing the present invention, and in particular, the operation of the peristaltic pumps 40 and 50. Larger fluid volumes in the reservoir 60 require correspondingly greater pumping forces to be applied by the supply-side peristaltic pump 40 to pump fluid thereinto. Likewise, larger volumes of fluid will apply correspondingly greater fluid pressures downstream upon the dispense-side peristaltic pump 50.

A typical optical detector will generally comprise a light source and a light receiver, either combined within a single unit or paired and assembled in close proximity. The light source supplies an optical signal (e.g. a beam or pulse or fan of collimated or coherent light) that is propagated along an optical pathway—linear or otherwise—that terminates at said light receiver after incidence upon said side tube 16. The light receiver is provided with a photoreceptor (e.g., a charge-coupled device) that provides an electronic signal corresponding with and in response to the light impinging thereon.

As indicated above, the fluid level in the pliable fluid reservoir 60 can also be monitored using—instead of optical fluid level sensors 52 and 54—electronic sensing mean. The electronic fluid level sensing means can be used to measure reservoir fluid levels directly from pliable fluid reservoir 60 or indirectly from a side tube 16.

Use of electronic fluid level sensing means involves the application of electroconductive terminals 18 (e.g., thin strip of conductive metal) onto the exterior surface of reservoir 60 or side tube 16. An electric current is passed from one terminal to another, and capacitance or resistance or the like is measured and a signal produced. Variations in capacitance or resistance can be correlated with variations in fluid level.

The electroconductive terminals by themselves are not sufficient to render operable the electronic fluid level sensing means. The electroconductive terminals need to be wired or otherwise linked or connected to both an energy source and an electronic control mechanism, both of which can be integrated within a single sub-component. The energy source essentially drives a current through both terminals, whilst the electronic control mechanism—for example, by incorporation therein of a potentiometer or like electronic sensor—measures the capacitance of said current and, based thereon, selectively opens and/or closes the relevant valves and/or pumps.

The electronic circuitry enabling the capacitance detection should be configured with an eye towards single-use disposability. Thus, for example, a consumable embodiment of the pliable fluid reservoir 60 can include the terminals, and perhaps some leads and wires, that are plugged into and/or otherwise connected to appropriate dedicated sockets into the non-disposable hardware components of the fluid filtration device 10.

In a particular embodiment, the electronic terminals comprise two narrow copper strips mounted permanently to the side wall of the side tube 16. The strips are mounted opposed to one another on the outside of the tube and traverse its entire "working" length. Capacitance detection is accomplished by passing a pulsed current across the space between the two metal strips. The capacitance of the material separating the strips is measured. Since there is a significant difference between the capacitance of an empty air-filled tube and one that is liquid filled, the liquid volume can be continually monitored as it move up and down the side tube.

Alternatives exist to the placement of the copper strips on the outside surface of the fill tube assembly. For example, the copper strips can be mounted as follows: One is mounted on the outside of the side tube (e.g., towards a bottom portion thereof) and the second is placed inside the tube assembly suspended without touching the walls. This embodiment is particularly appropriate for high viscosity fluids that tend to "cling" vigorously to the tube's side walls. To prevent unwanted chemical interaction between the internally mounted terminal and fluid loaded into the side tube assembly, the internally mounted terminal is preferably coated with a chemically non-reactive polymeric material or otherwise protected or isolated with some other suitable barrier.

In the operation of the host fluid dispensing apparatus, the capacitance in the fill tube assembly is measured continuously, so that the volume of in the tube will be continuously determined, rather than determining certain minimum and maximum volumes. Since the capacitance sensor measures the liquid continuously, so-called "proportional-integral-derivative" (PID) control of the system, rather than only proportional control, can be used thus improving the dispense accuracy and the repeatability.

As indicated, an electronic controller 90 is used to control the operation of the supply-side peristaltic pump 40 and/or the dispense-side peristaltic pump 50 based, at least in part, directly or indirectly, on the data (i.e., the signals) provided by the fluid level sensing mean 12. In one embodiment, as presently configured, the electronic controller 90 controls exclusively the operation of the supply-side peristaltic pump 40 based on data provided by the fluid level sensing means 12. In another embodiments, both pumps 40 and 50 are controlled by the electronic controller 90.

The electronic controller 90 should be capable of receiving, processing, and providing data at least to and from the sensing means 12 and either or both the peristaltic pumps 40 and 50. Similar functionality can be also provided for other potential device components, such as pinch valves, agitators, thermal sensors, data recording and printing devices, system displays, and the like.

The electronic controller 90 can comprise circuitry, wiring, memory modules, a power supply, input and output ports, a user interface, processors and co-processors, and other well-known electronic components to effect electronic connectivity and control of the serviced device components. The electronic controller can comprise either single centralized electronic package (e.g., a dedicated notebook computer or a multi-functional printed circuit board) or a network of distributed sub-components (e.g., a plurality of separate component-specific PCBs) wired or otherwise networked to a separate central processing unit.

A particular example of a distributed electronic controller system include a computer linked to an industrial programmable logic controller (i.e., a "PLC"), the programmable logic controller itself being linked to the electronically-controlled sensors and pumps. As known to those in the art, a programmable logic controller is essentially a device-specific computer board or component capable of electronically receiving, processing, and transmitting electronic data. The programmable logic controller operates with "raw" data and has embedded operating software therefor. The computer can be configured to communicate with, and to some extent control, the programmable logic controller, with higher level operations carried out by computer. Use of a programmable logic controller affords advantage in respect of easier replacement or substitution of a central device computer, as well as enabling broader variability in its selection.

While the invention has been described with reference to particular embodiments, it will be understood that the present invention is not limited to the particular constructions and methods herein disclosed and/or shown in the drawings, but also comprises any modifications or equivalents within the scope of the claims.

The invention claimed is:

1. A fluid dispensing device, suitable for dispensing fluid under atmospheric pressure from a fluid supply to a receptacle, comprising:
   a disposable single use pliable fluid reservoir having a fluid inlet and a fluid outlet;
   a pliable supply-side conduit connected to the fluid inlet of the pliable fluid reservoir to allow fluid to be sequentially squeezed therethrough;
   a pliable dispense-side conduit connected to the fluid outlet of the pliable fluid reservoir to allow fluid to be sequentially squeezed therethrough;
   sensing means placed proximate the pliable fluid reservoir, said sensing means capable of detecting the fluid level in the pliable fluid reservoir and transmitting data thereabout;
   a supply-side peristaltic pump engaged onto the supply-side conduit;
   a dispense-side peristaltic pump engaged onto the dispense-side conduit; and
   an electronic controller capable of controlling the supply-side and dispense-side peristaltic pumps based on data received from said sensing means.

2. The fluid dispensing device of claim 1, wherein either the supply-side peristaltic pump or the dispense-side peristaltic pump or both is a rotary peristaltic pump.

3. The fluid dispensing device of claim 1, wherein either the supply-side peristaltic pump or the dispense-side peristaltic pump or both is a linear peristaltic pump.

4. The fluid dispensing device of claim 1, wherein the pliable fluid reservoir has a substantially unitary construction, and is made from a material selected from the group consisting of polycarbonates, polyesters, nylons, PTFE, fluoropolymers, acrylics, methacrylics, acrylic copolymers, methacrylic copolymers, polysulphones, polyethersulphones, polyaryl-sulphones, polystryenes, polyvinyl chlorides, chlorinated polyvinyl chlorides, ABS blends, ABS alloys, polyurethanes, thermoset polymers, polyolefins, low density polyethylene, high density polyethylene, and ultrahigh molecular weight polyethylene, polyolefin copolymers, polypropylene, polypropylene copolymers, and metallocene generated polyolefins,
   wherein the pliable supply-side conduit and the pliable dispense-side conduit are each polymeric disposable single use conduits.

5. The fluid dispensing device of claim 4, wherein the pliable fluid reservoir is a bag of single-layer construction.

6. The fluid dispensing device of claim 1, further comprising a manifold assembly, said manifold assembly subdividing said dispense-side conduit into a plurality of sub-branches, each sub-branch being provided with its own said dispense-side peristaltic pump, whereby flow out of each sub-branch is individually enabled by each said dispense-side peristaltic pump.

7. The fluid dispensing device of claim 1, further comprising a manifold assembly and a plurality of electronically-controllable pinch valves, the manifold assembly sub-dividing said dispense-side conduit into a plurality of sub-branches, said dispense-side peristaltic pump being engaged onto said dispense-side conduit prior to the sub-division thereof by the manifold assembly, said pinch valves being engaged onto said sub-branches to enable control of flow therethrough.

8. A fluid dispensing device, suitable for dispensing fluid under atmospheric pressure, comprising:
   a peristaltic pump mechanism,
   a disposable single use pliable polymeric fluid reservoir,
   a disposable single use pliable supply-side conduit connected to the fluid inlet of the pliable fluid reservoir to allow fluid to be sequentially squeezed therethrough;
   a disposable single use pliable dispense-side conduit connected to the fluid outlet of the pliable fluid reservoir to allow fluid to be sequentially squeezed therethrough;
   a sensing means placed proximate the pliable polymeric fluid reservoir,
   means for engaging the pliable fluid reservoir; wherein
      (a) said pliable polymeric fluid reservoir has a fluid inlet and a fluid outlet, with a pliable polymeric supply-side conduit connected to the fluid inlet and a pliable polymeric dispense-side conduit connected to the fluid outlet;
      (b) the flow of fluid to and from said pliable polymeric fluid reservoir is driven at least in part by said peristaltic pump mechanism,
      (c) the sensing means is capable of detecting fluid level in the pliable polymeric fluid reservoir and transmitting data, and
      (d) an electronic controller capable of controlling the peristaltic pump mechanism based on data received from said sensing means,
   wherein each of the polymeric fluid reservoir, supply-side conduit, and dispense-side conduit are made from the same or different material selected from the group consisting of selected from the group consisting of polycarbonates, polyesters, nylons, PTFE, fluoropolymers, acrylics, methacrylics, acrylic copolymers, methacrylic copolymers, polysulphones, polyethersulphones, polyaryl-sulphones, polystryenes, polyvinyl chlorides, chlorinated polyvinyl chlorides, ABS blends, ABS alloys, polyurethanes, thermoset polymers, polyolefins, low density polyethylene, high density polyethylene, ultrahigh molecular weight polyethylene, polyolefin copolymers, polypropylene, polypropylene copolymers, and metallocene generated polyolefins.

9. The fluid-dispensing device of claim 8, wherein said peristaltic pump mechanism comprises a supply-side peristaltic pump engaged onto the supply-side conduit; and a dispense-side peristaltic pump engaged onto the dispense-side conduit.

10. The fluid dispensing device of claim 8, wherein a pre-sterilized pliable fluid reservoir is engaged into said fluid dispensing device.

11. The fluid dispensing device of claim 1, wherein sensing means is selected from the group consisting of an optical means, electroconductive means, sonic means, weighing means and combinations thereof.

12. A fluid dispensing device, suitable for dispensing fluid under atmospheric pressure from a fluid supply to a receptacle comprising:
   a single use pliable fluid reservoir having a fluid inlet, a fluid outlet, and gas gating means for maintaining atmospheric pressure throughout the device attached to the reservoir, above the maximum fluid level of the reservoir, for maintaining atmospheric pressure in the device;
   a pliable supply-side conduit connected to the fluid inlet of the fluid reservoir to allow fluid to be sequentially squeezed therethrough;
   a pliable dispense-side conduit connected to the fluid outlet of the fluid reservoir to allow fluid to be sequentially squeezed therethrough;
   sensing means placed proximate the fluid reservoir, wherein sensing means are capable of detecting the fluid level in the fluid reservoir and transmitting data thereabout;
   a supply-side peristaltic pump engaged onto the pliable supply-side conduit;
   a dispense-side peristaltic pump engaged onto the pliable dispense-side conduit;
   an electronic controller capable of controlling the supply-side and/or dispense-side peristaltic pumps based on data received from said sensing means;
   a manifold assembly; and
   a plurality of electronically-controllable pinch valves,
   wherein the manifold assembly sub-divides the pliable dispense-side conduit into a plurality of sub-branches, the dispense-side peristaltic pump being engaged onto the pliable dispense-side conduit prior to the sub-division thereof by the manifold assembly, and the pinch valves being engaged onto the sub-branches to enable control of flow therethrough.

13. The fluid dispensing device of claim 12, wherein sensing means is selected from the group consisting of an optical means, electroconductive means, sonic means, weighing means and combinations thereof.

14. The fluid dispensing device of claim 13, wherein sensing means is an optical detector comprising a side conduit in fluid communication with the pliable fluid reservoir and a plurality of optical detectors located proximate the side conduit to detect top and bottom fluid levels, respectively, along said side conduit which correlate with fluid levels in the pliable fluid reservoir.

15. The fluid dispensing device of claim 14, wherein sensing means is an electroconductive terminal comprising a side conduit in fluid communication with the pliable fluid reservoir and a plurality copper strips attached to the side conduit.

16. The fluid dispensing device of claim 12, wherein the fluid reservoir, fluid inlet, and fluid outlet are each made from the same or different pliable polymeric material selected from the group consisting of polycarbonates, polyesters, nylons, PTFE, fluoropolymers, acrylics, methacrylics, acrylic copolymers, methacrylic copolymers, polysulphones, polyethersulphones, polyaryl-sulphones, polystryenes, polyvinyl chlorides, chlorinated polyvinyl chlorides, ABS blends, ABS alloys, polyurethanes, thermoset polymers, polyolefins, low density polyethylene, high density polyethylene, ultrahigh molecular weight polyethylene, polyolefin copolymers, polypropylene, polypropylene copolymers, and metallocene generated polyolefins.

17. The fluid dispensing device of claim 12, wherein the gas gating means is selected from the group consisting of a vent filter assemblage and a pressure activated valve.

18. The fluid dispensing device of claim 1, wherein the reservoir further comprises a pressure activated valve attached to the reservoir for maintaining atmospheric pressure in the device.

19. The fluid dispensing device of claim 1, further comprising a vent filter assemblage attached to the reservoir, above the maximum fluid level of the reservoir, for maintaining atmospheric pressure in the device.

20. The fluid dispensing device of claim 8, wherein the reservoir further comprises a vent filter assemblage located above the maximum fluid level of the reservoir for maintaining atmospheric pressure in the device.

* * * * *